United States Patent [19]

Sarantakis

[11] 4,012,345

[45] Mar. 15, 1977

[54] DES-(ALA$^1$, GLY$^2$), MET$^{11}$-SRIF AND INTERMEDIATES

[75] Inventor: Dimitrios Sarantakis, West Chester, Pa.

[73] Assignee: American Home Products Corporation, New York, N.Y.

[22] Filed: Jan. 30, 1976

[21] Appl. No.: 654,147

[52] U.S. Cl. .................................. 260/8; 260/6; 260/112.5 S; 424/177
[51] Int. Cl.$^2$ ............... C07C 103/52; A61K 37/00; C08L 89/00
[58] Field of Search ............... 260/112.5 S, 78 A; 424/177

[56] References Cited

OTHER PUBLICATIONS

B520,514, Mar. 1976, Sarantakis, 260/112.5 S.

*Primary Examiner*—Lewis Gotts
*Assistant Examiner*—Reginald J. Suyat
*Attorney, Agent, or Firm*—Richard K. Jackson

[57] ABSTRACT

The dodecapeptide H-Cys-Lys-Asn-Phe-Phe-Trp-Lys-Thr-Met-Thr-Ser-Cys-OH, its oxidized form, D-Trp$^6$ analogue and intermediates obtained in their synthesis are described. These dodecapeptides inhibit the secretion of the hormone somatotropin (growth hormone).

8 Claims, No Drawings

DES-(ALA[1], GLY[2]), MET[11]-SRIF AND INTERMEDIATES

This invention relates to novel dodecapeptides and intermediates obtained in their synthesis by the solid phase method of peptide synthesis.

Somatostatin (also known as somatotropin release inhibiting factor or SRIF) is the tetradecapeptide

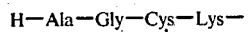
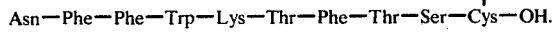

This tetradecapeptide has only recently been identified by isolation from extracts of ovine hypothalamic tissues and found to inhibit the secretion of the hormone somatotropin which is commonly referred to as the growth hormone (GH); See Brazeau et al., Science, 179 pp 77–79 (Jan. 1973). The linear form of this tetradecapeptide, H-Ala-Gly-Cys-Lys-Asn-Phe-Phe-Trp-Lys-Thr-Phe-Thr-Ser-Cys-OH, has also been reported by Brazeau et al., supra, to have been synthesized by solid phase methodology and found to have the same biological activity as somatostatin obtained from a natural source. The D-Trp[8] analogue of somatostatin is disclosed by Rivier et al. in Biochem, Biophys. Res. Comm., vol. 65, No. 2, pp. 746–751 (1975).

The novel dodecapeptides of the present invention are analogs of somatostatin and the linear counterpart of somatostatin in which the amino acids in the one and two positions of somatostatin have been omitted and L-methionyl replaces L-phenylalanyl in 9-position.

The dodecapeptides of the present invention which inhibit the secretion of the hormone somatotropin are represented by the formulas:

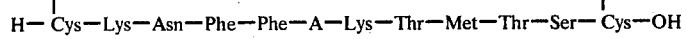

(I-cyclic or oxidized form)

and

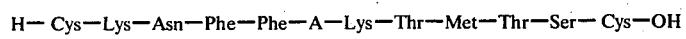

(II-linear form)

where A is L-tryptophyl or D-tryptophyl, and the non-toxic acid addition salts thereof. Illustrative of acid addition salts are hydrochloride, hydrobromide, sulfate, polyphosphate, phosphate, maleate, acetate, citrate, benzoate, succinate, malate, ascorbate and the like.

The nomenclature used to depict the peptides follow that shown is by Schroder & Lubke, "The Peptides," 1 pp viii–xxix (Academic Press 1965). All chiral amino acid residues identified in formulas I and II, supra, and the other formulas hereinafter are of the natural or L-configuration unless specified otherwise.

The present invention also relates to novel dodecapeptide intermediates of the formula:

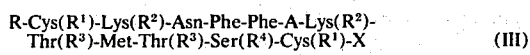

wherein:

A is L-tryptophyl or D-tryptophyl;

R is hydrogen, formyl, trifluoroacetyl, phthalyl, toluenesulfonyl, o-nitrophenylsulfenyl, benzyloxycarbonyl, p-methoxybenzyloxycarbonyl, p-nitrobenzyloxycarbonyl, 2-bromobenzyloxycarbonyl, 2-chlorobenzyloxycarbonyl, 1-(p-biphenylyl)-1-methyl-ethoxy carbonyl, tert-butyloxycarbonyl, diisopropylmethoxycarbonyl, allyloxycarbonyl, 2,2,2-trichloroethoxycarbonyl, amyloxycarbonyl, α,α-dimethylbenzyloxycarbonyl, α,α-dimethyl-3,5-dimethoxybenzyloxycarbonyl, benzhydryloxycarbonyl, 9-fluoroenylmethoxycarbonyl, isobornyloxycarbonyl, adamantyloxycarbonyl;

$R^1$ is a protecting group for the sulfhydryl group of the two cysteinyl moieties independently selected from the group consisting of benzyl, 3,4-dimethylbenzyl, p-methoxybenzyl, p-nitrobenzyl, p-chlorobenzyl, trityl, benzhydryl, tetrahydropyranyl, acetamidomethyl, t-butylthio, ethylthio, ethylcarbamoyl, benzylthiomethyl or benzoyl;

$R^2$ is formyl, trifluoroacetyl, phthalyl, toluenesulfonyl, o-nitrophenylsulfenyl, benzyloxycarbonyl, p-methoxybenzyloxycarbonyl, p-nitrobenzyloxycarbonyl, 2-bromobenzyloxycarbonyl, 2-chlorobenzyloxycarbonyl, 1-(p-biphenylyl)-1-methyl-ethoxy carbonyl, tert-butyloxycarbonyl, diisopropylmethoxycarbonyl, allyloxycarbonyl, 2,2,2-trichloroethoxycarbonyl, amyloxycarbonyl, α,α-dimethylbenzyloxycarbonyl, α,α-dimethyl-3,5-dimethoxybenzyloxycarbonyl, benzhydryloxycarbonyl, 9-fluorenylmethoxycarbonyl, isobornyloxycarbonyl, adamantyloxycarbonyl; The selection of such a side chain amino protecting group is not critical except that it must be one which is not removed during cleavage of the α-amino protecting group during the synthesis until the peptide of the desired amino acid sequence is obtained. Hence, the α-amino protecting and side chain amino protecting group cannot be the same;

$R^3$ and $R^4$ are protecting groups for the hydroxyl group of the threonyl and seryl moieties, independently selected from the group consisting of benzoyl, tert-butyl or benzyl. The preferred protecting group for $R^3$ and $R^4$ is benzyl. The selection of these protecting groups is not critical except that they must not be removed during cleavage of the α-amino protecting group during the synthesis until the peptide of the desired amino acid sequence is obtained;

X is selected from the group consisting of OH, $OCH_3$ and an anchoring bond used in solid phase synthesis linked to a solid resin support represented by the formula:

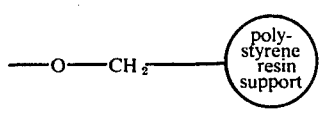

The polystyrene resin support is preferably a copolymer of styrene with about 1 to 2% divinyl benzene as a cross linking agent which causes the polystyrene polymer to be completely insoluble in certain organic solvents. The polystyrene polymer is composed of long alkyl chains bearing a phenyl ring on every second carbon and the terminal amino acid residue (Cys) is joined through a covalent carbon to oxygen bond to these phenyl rings. The alkyl chains are cross linked at approximately every fiftieth carbon by p-diethylphenyl residues derived from divinyl benzene.

In formula III, when X is OH, at least one of R, $R^1$, $R^2$, $R^3$ and $R^4$ is a protecting group.

In selecting a particular side chain protecting group to be used in the synthesis of the peptides of formulas I, II and III, the following rules should be followed: (a) the protecting group must be stable to the reagent and under the reaction conditions selected for removing the α-amino protecting group at each step of the synthesis; (b) the protecting group must retain its protecting properties (i.e. not be split off under coupling conditions, and (c) the side chain protecting group must be removable upon the completion of the synthesis containing the desired amino acid sequence under reaction conditions that will not alter the peptide chain.

The dodecapeptide peptide of formulas I, II and III are prepared using solid phase synthesis. The synthesis is commenced from the C-terminal end of the peptide using an α-amino protected resin. Such a starting material can be prepared by attaching an α-amino protected cysteine to a chloromethylated resin or a hydroxymethyl resin. The preparation of the hydroxymethyl resin is described by Bodanszky et al., Chem. Ind (London) 38, 1597–98 (1966). A chloromethylated resin is commercially available from Bio Rad Laboratories Richmond, California and the preparation of such a resin is described by Stewart et al., "Solid Phase Peptide Synthesis" (Freeman & Co. San Francisco 1969), Chapter 1, pp 1–6. The α-amino protected cysteine is coupled to the chloromethylated or hydroxymethyl resin with the aid of a carboxyl group activating compound such as described by Kapoor, J. Pharm. Sci. 59, pp 1–27 (1970) the disclosure of which is incorporated herein by reference. Following the coupling of the α-amino protected cysteine to the resin support, the α-amino protecting group is removed such as by using trifluoroacetic acid in methylene chloride, trifluoroacetic acid alone or HCl in dioxane. The deprotection is carried out at a temperature between about 0° C. and room temperature. Other standard cleaving reagents and conditions for removal of specific α-amino protecting groups may be used as described in Schroder & Lubke, supra, 1 pp 72–75. After removal of the α-amino protecting group the remaining α-amino protected amino acids are coupled step-wise in the desired order to obtain a compound of formula III. However, as an alternate to adding each amino acid separately to the reaction, some of them may be coupled prior to addition to the aolid phase reactor. Each protected amino acid or amino acid sequence, is introduced into the solid phase reactor in about a four-fold excess and the coupling is carried out in a medium of dimethylformamide: methylene chloride (1:1) or in dimethylformamide or methylene chloride alone. In cases where incomplete coupling occurred the coupling procedure is repeated before removal of the α-amino protecting group, prior to the coupling of the next amino acid to the solid phase reactor. The success of the coupling reaction at each stage of the synthesis is monitored by the ninhydrin reaction as described by E. Kaiser et al., Analyt. Biochem, 34, 595 (1970).

After the desired amino acid sequence of formula III has been synthesized, the peptide is removed from the resin support by treatment with a reagent such as hydrogen fluoride which not only cleaves the peptide from the resin but also cleaves all remaining side chain protecting groups $R^1$, $R^2$, $R^3$ and $R^4$ and the α-amino protecting group R on cysteine to obtain directly a compound of formula II. As an alternate route, the dodecapeptide linked to the resin support may be separated from the resin by methanolysis after which the recovered C-terminal methyl ester is converted to the acid by hydrolysis. Any side chain protecting group may then be cleaved by the procedure previously described or by other procedures such as catalytic reduction (eg. Pd on $BaSO_4$) using conditions which will keep the Trp moiety intact. When using hydrogen fluoride for cleaving, anisole is included in the reaction vessel to prevent the oxidation of labile amino acid (e.g. tryptophan). The compounds of formula II are converted to compounds of formula I by air oxidation.

The solid phase synthesis procedure discussed supra, is well known in the art and has been essentially described by M. Monahan et al, C. R. Acad. Sci. Paris, 273, 508 (1971).

The following examples are illustrative of the preparation of the compounds of formulas I, II and III.

EXAMPLE 1

The preparation of t-butyloxycarbonyl-S-p-methoxybenzyl-L-cysteine Resin

A solution of the cesium salt of t-butyloxycarbonyl-S-p-methoxybenzyl-L-cysteine (25 m moles) in dimethylformamide is stirred with chloromethylated polystyrene resin (Bio-Beads X–XI, 200–400 mesh, 30 g.) at 50° C. for 16 hours. The resin is then separated by filtration and washed with dimethylformamide, 10 percent water in dimethylformamide, ethanol and dimethylformamide (1:9 v/v), dimethylformamide, methylene chloride, and methanol. The resin, after drying in vacuo over KOH is found to be substituted to the extent of 0.40 m moles of cysteine per gram of resin.

EXAMPLE 2 t-butyloxycarbonyl-S-p-methoxybenzyl-L-cysteinyl-ε-2-chlorobenzyloxycarbonyl
L-lysyl-L-asparaginyl-L-phenylalanyl-L-phenylalanyl-L-Trp-ptophyl-ε-2-chlorobenzyloxycarbonyl-L-lysyl-O-benzyl-L-threonyl-L-methionyl-O-benzyl-L-threonyl-O-benzyl-L-serine-s-p-methoxy-benzyl-L-cysteine resin The t-butyloxycarbonyl-S-p-methoxybenzyl-L-cysteine resin (8 g.) of Example 1 is placed in a Merrifield vessel and treated according to schedule A for the incorporation of, Boc-Ser(Bzl)OH, Boc-Thr(Bzl)OH, Boc-Met-OH, Boc-Thr(Bzl)OH, Boc-Lys(ClZ), Boc-Trp-OH or Boc-D-Trp-OH to produce the D-Trp isomer, Boc-Phe-OH, Boc-Phe-OH, Boc-Asn-OH, Boc-Lys(ClZ)OH and Boc-Cys(SMBzl)OH.

SCHEDULE A

1. Wash with $CH_2Cl_2 \times 3$
2. Treat with trifluoroacetic acid-$CH_2Cl_2$-1,2-ethane dithiol (1:1:0.5%) for 5 minutes
3. Treat with trifluoroacetic acid-$CH_2Cl_2$-1,2-ethane dithiol (1:1:0.5%) for 25 minutes
4. Wash with $CH_2Cl_2 \times 3$
5. Wash with dimethylformamide
6. Treat with 12% triethylamine in dimethylformamide twice for 3 minutes.
7. Wash with dimethylformamide
8. Wash with $CH_2Cl_2 \times 3$
9. Treat with 4 equivalents of the corresponding amino acid derivatives and 4 equivalents of N-hydroxybenzotriazole in $CH_2Cl_2$-dimethylformamide and stir for 5 minutes. In the case of Boc-Asn-OH, 8 equivalents of N-hydroxybenzotriazole are added
10. Add in two portions 5 equivalents of dicyclohexylcarbodiimide dissolved in $CH_2Cl_2$ and over a period of 30 minutes. Reaction time 18 hours.
11. Wash with dimethylformamide $\times 3$
12. Wash with $CH_2Cl_2 \times 3$
13. Test ninhydrin reaction according to Kaiser et al., Annal. Biochem. 34, 595 (1970). In case of incomplete reactions repeat lines 9 to 14 as above.

The resulting resin Boc-Cys(SMBzl)-Lys(ClZ)-Asn-Phe-Phe-Trp-Lys(ClZ)-Thr(Bzl)-Met-Thr(Bzl)-Ser(Bzl)-Cys(SMBzl)-O-Resin is analyzed.

Amino acid analysis: Asp (1) 1.07, Thr (2) 1.90, Ser (1) 0.68, Met (1) 0.89, Phe (2) 2, Lys (2)1.89, Cys, Trp. N.D.

EXAMPLE 3

L-Cysteinyl-L-lysyl-L-asparaginyl-L-phenylalanyl-L-phenylalanyl-L-tryptophyl-L-lysyl-L-threonyl-L-methionyl-L-threonyl-L-seryl-L-cysteine (1-12) disulfide The peptidoresin of the previous example (15 g.) was mixed with anisole (ea. 20 ml.) and treated with liquid HF (ca. 200 ml.) in vacuo for 30 minutes in an ice-bath. The excess HF was removed as fast as possible and the residue was extracted with 2 M AcOH (ca. 150 ml.). The aqueous solution was diluted with dearated water to 3,000 ml. and the pH brought to 7.2 with aq. $NH_4OH$ then left to stand in the cold room for 3 days. The solution was acidified with glacial AcOH to pH 6.5 and lyophilized then the crude product was chromatographed through a Sephadex G-25 column (2.5 × 150 cm.) and eluted with 2 M AcOH. Two overlapping peaks emerged and the slower moving one was pooled and evaporated in vacuo. The residue was passed again through a Sephadex G-25 (2.5 × 150 cm.) column as before to give a symmetrical peak between 561 ml. 700 ml. Yield 1.1 g.

Amino acid analysis Asp (1) 0.90, Thr (2) 2.09, Ser (1) 0.96, Met (1) 1.08, Phe (2) 2, Lys (2) 2, Trp, Cys, N.D.

The in vivo activity of the compounds of this invention was established by subjecting des-(Ala[1], Gly[2]), Met[11]-Somatostatin, as a representative compound of the invention, to the following standard test procedure: Three groups of ten albino male rats were arranged to provide a control group, a group for observation of Somatostatin activity as the standard and a group for the study of the test compound des-(Ala[1], Gly[2]), Met[11]-Somatostatin. Nembutal (50 mg/kg) was injected intraperitoneally into each rat. Fifteen minutes later a subcutaneous injection of the test compound, somatostatin and physiological saline (control) was administered separately to each of the three groups of rats. Ten minutes later 0.5 milliliters of arginine (300 mg/ml, pH 7.2) was injected into the rats heart. The rats were decapitated five minutes later and their blood was collected in Trasylol -EDTA. Aliquot samples were radioimmunoassayed for growth hormone and insulin. The results of these tests are presented below:

| Experiment | Compound | Dose µg/kg | GH ng/ml | Insulin µU/ml |
|---|---|---|---|---|
| 1 | Control | — | 97 ± 20 | 172 ± 11 |
|   | Example 3 | 400 | 28* ± 6 | 143 ± 13 |
|   | SRIF | 200 | 30* ± 4 | 114* ± 9 |
| 2 | Control | — | 176 ± 29 | |
|   | Example 3 | 100 | 72 ± 12* | |
|   | SRIF | 100 | 44 ± 7* | |
| 3 | Control | — | 123 ± 16 | 206 ± 19 |
|   | Example 3 | 1500 | 42 ± 10* | 128 ± 13 |
|   | SRIF | 200 | 62 ± 14* | 152 ± 25 |

*p < 0.01

Thus, the compounds of this invention are effective substitutes for somatostatin in the treatment of excessive secretion of somatotropin in domestic animals and for the control of the immuno-reactive pituitary growth hormone in comparative and experimental pharmacology. From the known relationship between growth hormone control in standard experimental animals and the human, the activity of the disclosed tetradecapeptide amides characterizes the compounds as useful in the treatment of acromegaly and juvenile diabetes in the same manner as somatostatin itself. Administration of the tetradecapeptide amides may be by conventional routes common to somatostatin and related polypeptides, under the guidance of a physician in an amount dictated by the extent of the dysfunction as determined by the physician. The compounds may be administered alone or in conjunction with conventional pharmaceutically acceptable carriers and adjuvants, in unit dosage form containing from about 2 to about 100 milligrams per kilogram host body weight.

If the active ingredient is administered in tablet form the tablet may contain: a binder such as gum tragacanth, corn starch, gelatin, an excipient such as dicalcium phosphate; a disintegrating agent such as corn starch, alginic acid, etc.; a lubricant such as magnesium stearate; and a sweetening and/or flavoring agent such as sucrose, lactose, wintergreen, etc. Suitable liquid carriers for intravenous administration include isotonic saline, phosphate buffer solutions, etc.

What is claimed is:

1. A dodecapeptide selected from those of the formula

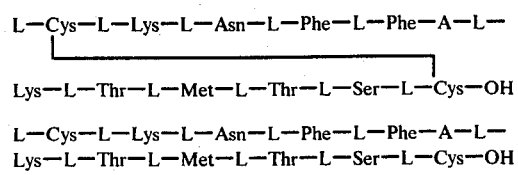

L—Cys—L—Lys—L—Asn—L—Phe—L—Phe—A—L—
Lys—L—Thr—L—Met—L—Thr—L—Ser—L—Cys—OH

L—Cys—L—Lys—L—Asn—L—Phe—L—Phe—A—L—
Lys—L—Thr—L—Met—L—Thr—L—Ser—L—Cys—OH in which
A is D-tryptophyl of L-tryptophyl and the non-toxic acid addition salts thereof.

2. A peptide according to claim 1 which is: L-Cysteinyl-L-lysyl-L-asparaginyl-L-phenylalanyl-L-phenylalanyl-L-tryptophy-L-lysyl-L-threonyl-L-methionyl-L-threonyl-L-seryl-L-cysteine and a non-toxic acid addition salt thereof.

3. A peptide according to claim 1 which is: L-cysteinyl-L-lysyl-L-asparaginyl-L-phenylalanyl-L-phenylalanyl-D-tryptophyl-L-lysyl-L-threonyl-L-methionyl-L-threonyl-L-seryl-L-cysteine and a non-toxic acid addition salt thereof.

4. A peptide according to claim 1 which is: L-Cysteinyl-L-lysyl-L-asparaginyl-L-phenylalanyl-L-phenylalanyl-L-tryptophyl-L-lysyl-L-threonyl-L-methionyl-L-threonyl-L-seryl-L-cysteine (cyclic 1, 12 disulfide) and a non-toxic acid addition salt thereof.

5. A peptide according to claim 1 which is: L-Cysteinyl-L-lysyl-L-asparaginyl-L-phenylalanyl-L-phenylalanyl-D-tryptophyl-L-lysyl-L-threonyl-L-methionyl-L-threonyl-L-seryl-L-cysteine (cyclic 1, 12 disulfide) and a non-toxic acid addition salt thereof.

6. A compound of the formula

R-L-Cys($R^1$)-L-Lys($R^2$)-L-Asn-L-Phe-L-Phe-A-L-Lys($R^2$)-L-Thr($R^3$)-L-Met-L-Thr($R^3$)-L-Ser($R^4$)-L-Cys($R^1$)-X wherein:

A is L-tryptophyl or D-tryptophyl

R is hydrogen, formyl, trifluoroacetyl, phthalyl, toluenesulfonyl, o-nitrophenylsulfenyl, benzyloxycarbonyl, p-methoxybenzyloxycarbonyl, p-nitrobenzyloxycarbonyl, 2-bromobenzyloxycarbonyl, 2-chlorobenzyloxycarbonyl, 1-(p-biphenylyl)-1-methyl-ethoxy carbonyl, tert-butyloxycarbonyl, diisopropylmethoxycarbonyl, allyloxycarbonyl, 2,2,2-trichloroethoxycarbonyl, amyloxycarbonyl, α,α-dimethylbenzyloxycarbonyl, α,α-dimethyl-3,5-dimethoxybenzyloxycarbonyl, benzhydryloxycarbonyl, 9-fluoroenylmethoxycarbonyl, isobornyloxycarbonyl, adamantyloxycarbonyl;

$R^1$ is a protecting group for the sulfhydryl group of the two cysteinyl moieties independently selected from the group consisting of benzyl, 3,4-dimethylbenzyl, p-methoxybenzyl, p-nitrobenzyl, p-chlorobenzyl, trityl, benzhydryl, tetrahydropyranyl, acetamidomethyl, t-butylthio, ethylthio, ethylcarbamoyl, benzylthiomethyl or benzoyl;

$R^2$ is formyl, trifluoroacetyl, phthalyl, toluenesulfonyl, o-nitrophenylsulfenyl, benzyloxycarbonyl, p-methoxybenzyloxycarbonyl, p-nitrobenzyloxycarbonyl, 2-bromobenzyloxycarbonyl, 2-chlorobenzyloxycarbonyl, 1(p-biphenylyl)-1-methyl-ethoxy carbonyl, tert-butyloxycarbonyl, diisopropylmethoxycarbonyl, allyloxycarbonyl, 2,2,2-trichloroethoxycarbonyl, amyloxycarbonyl, α,α-dimethylbenzyloxycarbonyl, α,α-dimethyl-3,5-dimethoxybenzyloxycarbonyl, benzhydryloxycarbonyl, 9-fluoroenylmethoxycarbonyl, isobornyloxycarbonyl, adamantyloxycarbonyl;

$R^3$ and $R^4$ are protecting groups for the hydroxyl group of the threonyl and seryl moieties, independently selected from the group consisting of benzoyl, tert-butyl, benzyl. The preferred protecting group for $R^3$ and $R^4$ is benzyl;

X is selected from the group consisting of OH, $OCH_3$ and an anchoring bond used in solid phase synthesis linked to a solid resin support represented by the formula

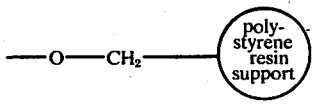

said protecting groups defined by $R^1$, $R^2$, $R^3$ and $R^4$ being capable of being split off chemically under conditions that do not cleave said peptide chain and at least one of R, $R^1$, $R^2$, $R^3$ and $R^4$ being a protecting group when X is OH.

7. A compound according to claim 6 wherein X is

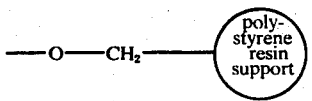

8. A compound according to claim 7 wherein R is t-butyloxycarbonyl, $R^1$ is p-methoxybenzyl, $R^2$ is benzyloxycarbonyl, $R^3$ is benzyl and $R^4$ is benzyl.

* * * * *